United States Patent
Daly et al.

(10) Patent No.: US 12,421,501 B2
(45) Date of Patent: Sep. 23, 2025

(54) CHEMICALLY DEFINED DIFFERENTIATION PROTOCOL FOR PERICYTE DIFFERENTIATION FROM PLURIPOTENT STEM CELLS

(71) Applicant: Wisconsin Alumni Research Foundation, Madison, WI (US)

(72) Inventors: William T. Daly, Madison, WI (US); William L. Murphy, Waunakee, WI (US); Cheryl M. Soref, Madison, WI (US); Elizabeth E. Torr, Madison, WI (US); Elizabeth A. Aisenbrey, Madison, WI (US); Hunter J. Johnson, Brooklyn, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 621 days.

(21) Appl. No.: 16/385,543

(22) Filed: Apr. 16, 2019

(65) Prior Publication Data
US 2019/0316094 A1     Oct. 17, 2019

Related U.S. Application Data

(60) Provisional application No. 62/658,042, filed on Apr. 16, 2018.

(51) Int. Cl.
C12N 5/071 (2010.01)
C12N 5/00 (2006.01)
G01N 33/50 (2006.01)

(52) U.S. Cl.
CPC ......... *C12N 5/0691* (2013.01); *C12N 5/0062* (2013.01); *C12N 5/0068* (2013.01);
(Continued)

(58) Field of Classification Search
CPC .. C12N 5/0691; C12N 5/0062; C12N 5/0068; C12N 2501/115; C12N 2501/155; C12N 2501/16; C12N 2501/165; C12N 2501/33; C12N 2501/998; C12N 2501/999; C12N 2506/02; C12N 2506/45; C12N 2513/00;
(Continued)

(56) References Cited

U.S. PATENT DOCUMENTS

| | | | |
|---|---|---|---|
| 5,843,780 A | 12/1998 | Thomson | |
| 2014/0369968 A1* | 12/2014 | Slukvin | A61K 35/44 424/93.7 |
| 2016/0244719 A1* | 8/2016 | Thomson | G01N 33/5064 |

OTHER PUBLICATIONS

Zimmerlin et al ("Pericytes: a Ubiquitous Source of Multipotent Adult Tissue Stem Cells," Chapter 9, Stem Cells in Aesthetic Procedures, 135-148, Springer-Verlag Berlin Heidelberg 2014, M.A. Shiffman et al. (eds.). (Year: 2014).*

(Continued)

*Primary Examiner* — Tracy Vivlemore
*Assistant Examiner* — Lauren K Van Buren
(74) *Attorney, Agent, or Firm* — Quarles & Brady, LLP

(57) ABSTRACT

The present invention provides methods of differentiating pericytes from pluripotent stem cells comprising culturing steps in chemically defined culture medium. A population of exogenously derived pericytes from PSCs are also contemplated. Further uses of the exogenously cultured pericytes for an in vitro disease model or in vitro angiogenesis assay are contemplated, including an in vitro 3D model of vasculature.

12 Claims, 6 Drawing Sheets
(6 of 6 Drawing Sheet(s) Filed in Color)

(52) U.S. Cl.
CPC .... *G01N 33/5005* (2013.01); *C12N 2501/115* (2013.01); *C12N 2501/155* (2013.01); *C12N 2501/16* (2013.01); *C12N 2501/165* (2013.01); *C12N 2501/33* (2013.01); *C12N 2501/998* (2013.01); *C12N 2501/999* (2013.01); *C12N 2506/02* (2013.01); *C12N 2506/45* (2013.01); *C12N 2513/00* (2013.01); *C12N 2533/52* (2013.01); *C12N 2533/54* (2013.01)

(58) Field of Classification Search
CPC ............ C12N 2533/52; C12N 2533/54; C12N 5/0692; C12N 2500/25; C12N 2501/119; G01N 33/5005
See application file for complete search history.

(56) References Cited

OTHER PUBLICATIONS

Zimmerlin et al ("Mesenchymal Markers on Human AdiposeStem/Progenitor Cells," Cytometry Part A83A: 134-140, 2013) (Zimmerlin2). (Year: 2013).*
Lee "Inhibitor of pluripotent stem cell derived teratoma formation by small molecules" PNAS, e281-e3290 (Year: 2013).*
Armulik, et al., Pericytes regulate the blood-brain barrier. Nature 2010. 468:557-561.
Beltramo, et al., Pericyte Loss in Diabetic Retinopathy: Mechanisms and Consequences. Med Chem 2013. 20(26):3218-3225.
Bergers, et al., Modes of resistance to anti-angiogenic therapy. Nat. Rev. Cancer 2008. 8(8):592-603.
Bergers, et al., The role of pericytes in blood-vessel formation and maintenance. Neuro-Oncol. 2005. 7:452-464.
Bianciardi, et al., Microvascular abnormalities in Rett syndrome. Clin. Hemorheol. Microcirc. 2013. 54:109-113.
Blocki, et al., Not All MSCs Can Act as Pericytes: Functional In Vitro Assays to Distinguish Pericytes from Other Mesenchymal Stem Cells in Angiogenesis. Stem Cells Dev. 2013. 22(17):2347-2355.
Caballero, et al., MeCP2 in neurons: closing in on the causes of Rett syndrome. Hum. Mol. Genet. 2005. 14:19-26.
Chen, et al., Role of pericytes in angiogenesis: focus on cancer angiogenesis and anti-angiogenic therapy. Neoplasma 2016. 63(2):173-182.
Cheng, et al., Targeting pericytes for therapeutic approaches to neurological disorders. Acta Neuropathol. 2018. 136(4):507-523.
Cheung, et al., Directed differentiation of embryonic origin-specific vascular smooth muscle subtypes from human pluripotent stem cells. Nat Protoc. 2014. 9(4):929-38.
Cheung, et al., Modeling cerebrovascular pathophysiology in amyloid-β metabolism using neural-crest-derived smooth muscle cells. Cell Rep. 2014. 9(1):391-401.
Dar, et al., Multipotent Vasculogenic Pericytes From Human Pluripotent Stem Cells Promote Recovery of Murine Ischemic Limb. Circulation 2012. 125:87-99.
Enge, et al., Endothelium-specific platelet-derived growth factor-B ablation mimics diabetic retinopathy. EMBO J. 2002. 21(16):4307-4316.
Ferland-McCollough, et al., Pericytes, an overlooked player in vascular pathobiology. Pharmacol. Ther. 2017. 171:30-42.
Gerhardt, et al., Pericytes: gatekeepers in tumour cell metastasis? J. Mol. Med. 2008. 86:135-144.
Greenwood-Goodwin, et al., A novel lineage restricted, pericyte-like cell line isolated from human embryonic stem cells. Sci. Rep. 2016. 6:24403.
Guy, et al., Reversal of Neurological Defects in a Mouse Model of Rett Syndrome. Science 2007. 315(5815):1143-1147.
Hellström, et al., Lack of Pericytes Leads to Endothelial Hyperplasia and Abnormal Vascular Morphogenesis. Cell Biol. 2001. 153(3):543-553.

Keating, et al., Mesenchymal Stromal Cells: New Directions. Cell Stem Cell 2012. 10(6):709-716.
Kim, et al., Perivascular Progenitor Cells Derived From Human Embryonic Stem Cells Exhibit Functional Characteristics of Pericytes and Improve the Retinal Vasculature in a Rodent Model of Diabetic Retinopathy Stem Cells. Transl. Med. 2016. 5:1268-1276.
Kumar, et al., Specification and Diversification of Pericytes and Smooth Muscle Cells from Mesenchymoangioblasts. Cell Rep. 2017. 19(9):1902-1916.
Lappalainen, et al., Brain perfusion SPECT and EEG findings in Rett syndrome. Neurol. Scand. 1997. 95(1):44-50.
Laurvick, et al., Rett syndrome in Australia: a review of the epidemiology. J. Pediatr. 2006. 148(3):347-352.
Lee, et al., Isolation and directed differentiation of neural crest stem cells derived from human embryonic stem cells. Nat. Biotech. 2007. 25(12):1468-1475.
Lee, et al., Derivation of neural crest cells from human pluripotent stem cells. Nat. Protoc. 2010. 5(4):688-701.
Menendez, et al., Directed differentiation of human pluripotent cells to neural crest stem cells. Nat Protoc. 2013. 8(1):203-212.
Menendez, et al., Wnt signaling and a Smad pathway blockade direct the differentiation of human pluripotent stem cells to multipotent neural crest cells. PNAS 2011. 108(48):19240-5.
Neul, et al., Specific Mutations in Methyl-CpG-Binding Protein 2 Confer Different Severity in Rett Syndrome. Neurology 2008. 70(16):1313-1321.
Nikolakopoulou, et al., Regional early and progressive loss of brain pericytes but not vascular smooth muscle cells in adult mice with disrupted platelet-derived growth factor receptor-β signaling. PLOS ONE 2017. 12:e0176225.
Orlova, et al., Functionality of Endothelial Cells and Pericytes From Human Pluripotent Stem Cells Demonstrated in Cultured Vascular Plexus and Zebrafish Xenografts. Arterioscler. Thromb. Vasc. Biol. 2014. 34:177-186.
Orlova, et al., Generation, expansion and functional analysis of endothelial cells and pericytes derived from human pluripotent stem cells. Nat. Protoc. 2014. 9:1514-1531.
Özen, et al., Brain pericytes acquire a microglial phenotype after stroke. Acta Neuropathol. 2014. 128(3):381-396.
Özen, et al., Perivascular mesenchymal stem cells in the adult human brain: a future target for neuroregeneration? Clin. Transl. Med. 2012. 1:30.
Paiva, et al., Pericytes in the Premetastatic Niche. Cancer Res. 2018. 78(11):2779-2786.
Pallone, et al., Pericyte Regulation of Renal Medullary Blood Flow. Exp. Nephrol. 2001. 9(3):165-170.
Panighini, et al., Vascular Dysfunction in a Mouse Model of Rett Syndrome and Effects of Curcumin Treatment. PLoS ONE 2013. 8(5):e64863.
Paul, et al., The Adult Human Brain Harbors Multipotent Perivascular Mesenchymal Stem Cells. PLOS ONE 2012. 7(4):e35577.
Pettinato, et al., Engineering Strategies for the Formation of Embryoid Bodies from Human Pluripotent Stem Cells. Stem Cells Dev. 2015. 24(14):1595-1609.
Reubinoff, et al., Embryonic stem cell lines from human blastocysts: somatic differentiation in vitro. Nature Biotech 2000. 18:399-404.
Ricceri, et al., Mouse models of Rett syndrome: from behavioural phenotyping to preclinical evaluation of new therapeutic approaches. Behav. Pharmacol. 2008. 19:501-517.
Schwartz, et al., Human pluripotent stem cell-derived neural constructs for predicting neural toxicity. PNAS 2016. (112) 40, pp. 12516-12521.
Shepro, et al., Pericyte physiology. FASEB J. 1993. 7(11):1031.
Smeets, et al., Rett Syndrome. Mol. Syndromol. 2012. 2:113-127.
Sorrell, et al., Influence of Adult Mesenchymal Stem Cells on In Vitro Vascular Formation. Tissue Eng. Part A 2009 15(7):1751-1761.
Stenberg, et al., Sustained embryoid body formation and culture in a non-laborious three dimensional culture system for human embryonic stem cells. Cytotechnology 2011. 63(3):227-237.
Thomas, Brain macrophages: on the role of pericytes and perivascular cells. Brain Res. Rev. 1999. 31(1):42-57.

(56) References Cited

OTHER PUBLICATIONS

Thomsen, et al., Synthesis and deposition of basement membrane proteins by primary brain capillary endothelial cells in a murine model of the blood-brain barrier. J. Neurochem. 2017. 140:741-754.
Van Beijnum, et al., The Great Escape; the Hallmarks of Resistance to Antiangiogenic Therapy Pharmacol. Rev. 2015. 67:441-461.
Wang, et al., MeCP2-mediated epigenetic regulation in senescent endothelial progenitor cells. Stem Cell Res. Ther. 2018. 9:87.
Winkler, et al., Pericyte-specific expression of PDGF beta receptor in mouse models with normal and deficient PDGF beta receptor signaling. Mol. Neurodegener. 2010. 5:32.
Xian, et al., Pericytes limit tumor cell metastasis. J. Clin. Invest. 2006. 116(3):642-651.
Xu, et al., A systematic review: differentiation of stem cells into functional pericytes. FASEB J. 2017. 31:1775-1786.
Yamamizu, et al., In Vitro Modeling of Blood-Brain Barrier with Human iPSC-Derived Endothelial Cells, Pericytes, Neurons, and Astrocytes via Notch Signaling. Stem Cell Reports 2017. 8:1-14.
Zhang, et al., PI3K/AKT/mTOR Signaling Mediates Valproic Acid-Induced Neuronal Differentiation of Neural Stem Cells through Epigenetic Modifications. Stem Cell Reports 2017. 8(5):1256-1269.

\* cited by examiner

CHEMICALLY DEFINED DIFFERENTIATION PROTOCOL FOR PERICYTE DIFFERENTIATION FROM PLURIPOTENT STEM CELLS

CROSS-REFERENCE TO RELATED APPLICATIONS

This application claims priority to U.S. Provisional Application No. 62/658,042 filed on Apr. 16, 2018, the contents of which are incorporated by reference in its entirety.

STATEMENT REGARDING FEDERALLY SPONSORED RESEARCH

This invention was made with government support under TR000506 awarded by the National Institutes of Health and RD-83573701-0 awarded by the Environmental Protection Agency. The government has certain rights in the invention.

BACKGROUND OF THE INVENTION

Most blood vessels are composed of three layers including a luminal inner monolayer of endothelial cells, an intermediate muscular layer of smooth muscle cells (SMC) and an outer layer of fibroblast-like, adventitial cells and connective tissue components. Microvessels, including capillaries, precapillary arterioles, metarterioles, postcapillary venules and collecting venules, are composed of an internal endothelial layer surrounded by outer coverage of pericytes.

Pericytes are perivascular contractile cells that are indispensable for normal blood vessel function by stabilizing maturing blood vessels, forming permeability barriers and regulating the blood flow. They also contribute to angiogenic sprouting and migrate to vascularizing tissues and tumors. Pericytes can be distinguished from SMC based on their characteristic morphology and specific cell marker expression. While SMC form a separate layer in blood vessels, pericytes wrap around the endothelial cells that line the capillaries and venules throughout the body and are physically embedded within the endothelial basement membrane to promote mutual communication with the underlying endothelium. Pericytes communicate with endothelial cells of small blood vessels by means of both direct physical contact and paracrine signaling. In the brain, pericytes help sustain the blood-brain barrier as well as several other homeostatic and hemostatic functions of the brain.

While pericytes can be purified from tissue homogenates (e.g., placenta, muscle, etc.) and under complicated in vitro methods, there is a need for simple in vitro methods of generating large populations of pericytes for use in disease models and for therapeutic purposes.

SUMMARY OF THE INVENTION

In one aspect, the present disclosure provides a method of isolating pericytes from pluripotent stem cells, the method comprising: a) culturing pluripotent stem cells on coated plates in a chemically defined culture medium supplemented with about 1-30 ng/ml BMP4, about 10-30 ng/ml activin, and about 1-5 μM GSK-3 inhibitor for at least 2 days, b) culturing the cultured cells of step (a) in chemically defined medium supplemented with about 5-15 μg/ml transferrin, about 10-30 μg/ml insulin, about 70-150 ng/ml fibroblast growth factor 2 (FGF2), about 25-75 ng/ml vascular endothelial growth factor-A(165) (VEGF-A(165)), and about 2-10 μM TGFβ1 inhibitor to differentiate the cells into CD34− or CD31− cell population, c) detecting CD34− or CD31− cell population at day 6 of culture and isolating the CD34+ or CD31+ cells from the population, d) culturing the CD34− or CD31− cells in step (c) in EGM2 media for at least 2 days on coated plates; and e) detecting the pericyte markers PDGFRβ, SM22, CD13 and Desmin in a population of cultured pericyte cells of step (d), wherein the population is at least about 95% pure. In some aspects, the chemically defined medium of step (a) is E8 medium.

In some aspects, the pluripotent stem cells are induced pluripotent stem cells (iPSCs) or embryonic stem cells (ESCs).

In one aspect, the TGFβ1 inhibitor is SB431542. In another aspect, in step (a), the chemically defined medium is supplemented with about 5 ng/ml BMP4, about 25 ng/ml activin A and about 1 μM GSK-3 inhibitor, and in step (b), the chemically defined media is supplemented with about 10-11 ng/ml transferrin, about 20 ng/ml insulin, about 100 ng/ml FGF2, about 50 ng/ml VEGF-A (165), and about 5 μM TGFβ1 inhibitor.

In another aspect, the present disclosure provides a population of exogenously derived pericytes from PSCs made by the method described herein, wherein at least 95% of the population express PDGFRβ, SM22, CD13, and Desmin.

In another aspect, the present disclosure provides a method of isolating pericytes from CD34− or CD31− cell population, the method comprising: a) culturing a substantially pure population of CD34− or CD31− cells derived from PSCs in EGM2 media for at least 2 days on adherent substrate; and b) detecting the pericyte markers PDGFRβ, SM22, CD13 and Desmin on a population of cells, and isolating the population of pericytes expressing PDGFRβ, SM22, CD13 and Desmin.

BRIEF DESCRIPTION OF THE DRAWINGS

The patent or patent application file contains at least one drawing in color. Copies of this patent or patent application publication with color drawings will be provided by the Office upon request and payment of the necessary fee.

DETAILED DESCRIPTION OF THE INVENTION

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

A defined differentiation protocol for pluripotent stem cell derived pericytes remains a challenge in the field of stem cell bioengineering. Pericytes are important in the development and function of the human vascular system and are key components required to make vascularized 3D tissues. This is of particular importance for generating 3D vasculature and integrating this 3D vasculature with organoid models. Although independent laboratories have published protocols for pericyte differentiation, they are often difficult to reproduce due to use of non-standardized or complicated media formulations requiring extensive media supplementation (e.g. >14 factors with added serum and antibiotics). Efficiencies and purity of pericyte differentiations are often low and require the use of aggregate and embryoid bodies resulting in variations in their formation and are often indistinguishable from smooth muscle cells (SMCs) or a differentiated subpopulation of mesenchymal stem cells (MSCs).

Figure 1:
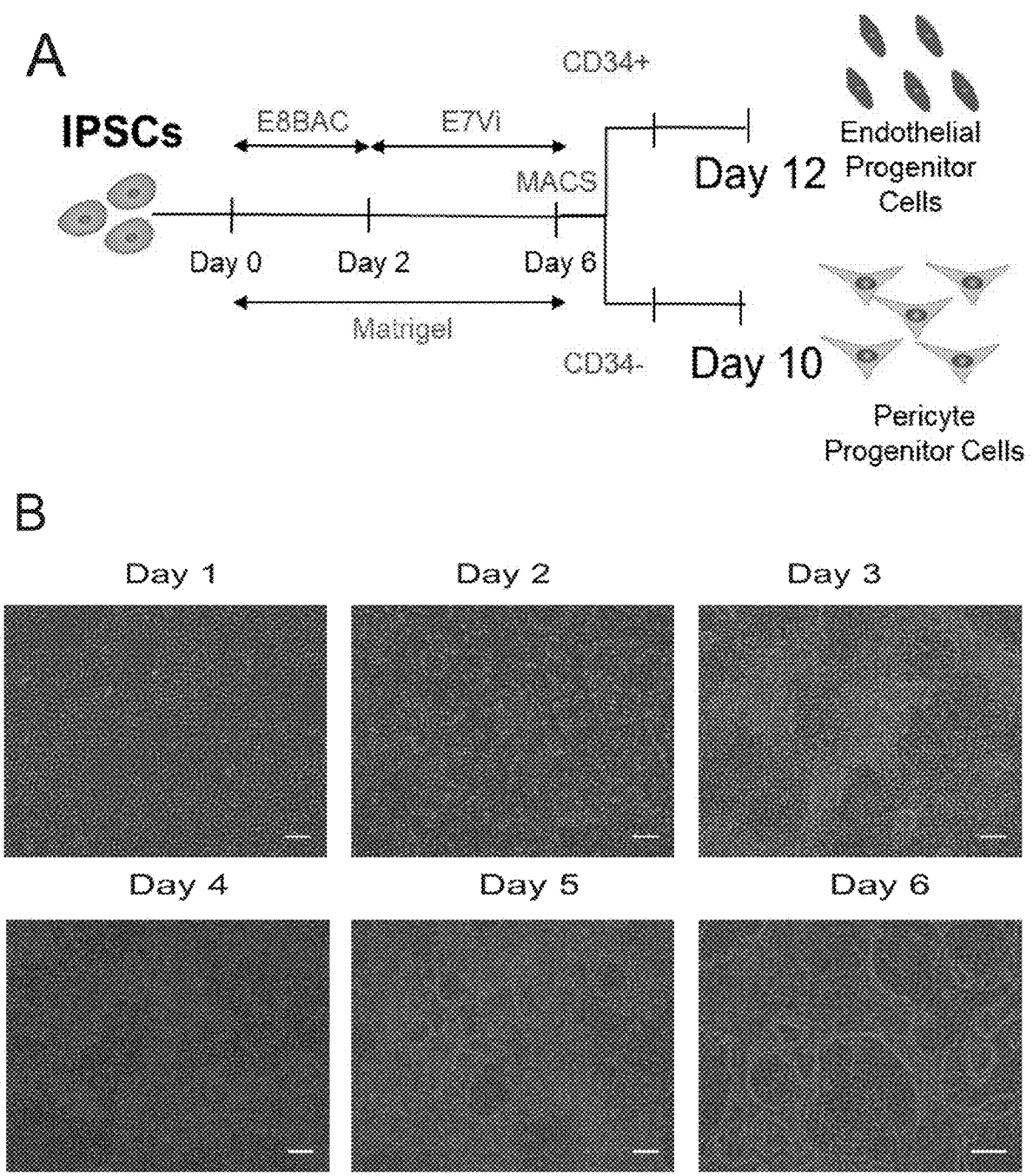
FIG. 1. The differentiation of induced pluripotent stem cells (iPSCs) to pericytes. (A) A schematic of the chemically defined differentiation protocol. (B) Representative brightfield images of WTC11 iPSCs differentiating into predominately endothelial progenitor cells and pericyte progenitor cells over the first 6-day differentiation timeline (scale bar=200 μm).

This disclosure provides methods of differentiating and cells differentiated in defined media (variations on standard E8 media) with minimal media supplementation in monolayer culture with a short differentiation timeline (less than 12 days, e.g., from 8-12 days) and result in high purity pericyte populations (e.g., at least 95% pure, alternatively at least 98% pure). The methods described can be used to differentiate both endothelial cells and pericytes from iPSCs in the same workflow, as depicted in FIG. 1A. The Examples below demonstrated that pericytes have been differentiated in vitro from multiple ESC and iPSC cell lines. Media formulations and material substrates have been optimized to increase the expression of pericyte markers and to prolong their ability to expand in culture.

In one embodiment, an in vitro method of differentiating pericytes from pluripotent stem cells is disclosed. The method comprises the steps of (a) culturing pluripotent stem cells in a monolayer on an adherent substrate in a first chemically defined culture medium (e.g., E8 medium) supplemented with about 1-30 ng/ml BMP4 (suitably 5 ng/ml), about 10-30 ng/ml activin (suitably 25 ng/ml) and about 1-5 µM GSK-3 inhibitor (suitably 1 µM of CHIR990221) for at least 2 days, and (b) subsequently culturing the cells on the first adherent substrate in a second chemically defined medium (e.g., DF3S medium, Thermo Fisher Scientific) supplemented with about 5-15 µg/ml transferrin (e.g., about 10.7 µg/ml), about 10-30 µg/ml insulin (e.g., about 20 µg/ml), about 70-150 ng/ml fibroblast growth factor 2 (FGF2) (e.g., about 100 ng/ml), about 25-75 ng/ml vascular endothelial growth factor-A(165) (VEGF-A(165)) (e.g., about 50 ng/ml) and about 2-10 µM TGFβ1 inhibitor (e.g., 5 µM SB431542) sufficient to differentiate the cells into CD34− or CD31− cells (pericyte precursor cells). CD34− or CD31− cells can be detected and isolated after about 6 days in culture (2 days culturing under step (a) and an additional 4 days under step (b)). After 6 days in culture, the CD34− or CD31− cells can be (c) detected and isolated from the cultured cell population. Alternatively, the V-cadherin-cell population can be detected and isolated in the above method. The derivation of the CD34− or CD31− cell population is a step that allows for the isolation of precursor cells able to differentiate into pericytes (PCs) from precursor cells that are able to differentiate into endothelial cells (e.g., cells that are CD34+ or CD31+ cells that are able to differentiate into endothelial cells). In some embodiments, a substantially pure population of CD34− or CD31− cells are isolated, e.g., at least 95% of the cells are CD34− or CD31−, alternatively at least 98% of the cells are CD34− or CD31−, alternatively at least 99% of the cells are CD34− or CD31−, alternatively 100% of the cells are CD34− or CD31−. Alternatively, a substantially pure population of V-cadherin-cells are isolated (e.g., 95% pure, alternatively 98% pure, alternatively 99% pure, alternatively 100% pure).

The method further comprises (d) culturing the CD34− or CD31− cells isolated in step (c) in a third chemically defined medium (e.g. EGM2 medium) for at least 2 days on a second adherent substrate to produce a pure population (e.g., at least 95%, alternatively at least 98%, alternatively at least 99%, alternatively 100%) pericytes. In some embodiments, the method further comprises detecting at least one of the pericyte markers PDGFRβ, SM22, CD13 and Desmin on a population of cells within the cultured cells of step (d). At this step, the population is a pure population of pericytes (e.g., at least 95%, alternatively at least 98%, alternatively at least 99%, alternatively 100% pericytes). In some embodiments, the method further comprises isolating the population of pericytes expressing PDGFRβ, SM22, CD13 and Desmin.

A pure population of pericytes, e.g., a population of at least 95% pericytes is produced by the method, alternatively at least 98% pericytes, alternatively at least 99% pericytes, alternatively 100% pericytes, is produced by the method described. A pure population of pericytes encompasses a cell population that expresses at least one pericyte marker on the cell surface of the cells, e.g., at least one of the cell surface markers PDGFRβ, SM22, CD13 and Desmin. In a preferred embodiment, the pure population of pericytes expresses two or more of the cell surface markers PDGFRβ, SM22, CD13 and Desmin, preferably three or more of the cell surface markers PDGFRβ, SM22, CD13 and Desmin, more preferably the cell surface markers PDGFRβ, SM22, CD13 and Desmin.

Adherent substrates suitable for use herein are not limited to any specific type and include any substrate that permits cells to attach and grow in monolayers, such as tissue culture plates coated with gelatin, or coated with an extracellular matrix protein such as fibronectin, vitronectin, laminin or those contained in a Matrigel™ coated plate. The term adherent substrates encompasses coated plates, specifically tissue culture coated plates. In a specific embodiment, the first adherent substrate used are Matrigel™ coated plates, and the second adherent substrate used are plates coated with gelatin, collagen IV, fibronectin or a mixture thereof. In a specific embodiment, the first adherent substrate is Matrigel™ coated plates and the second adherent substrate are plates coated with a mixture of collagen IV and fibronectin. In another embodiment, the first and second adherent substrate are Matrigel™ coated plates. In another embodiment, the first and second adherent substrate are vitronectin coated plates. In some embodiments, the first adherent substrate and second adherent substrate are selected from the group consisting of Matrigel™ coated plates, vitronectin coated plates, laminin coated plates, gelatin coated plates, collagen IV coated plates, fibronectin coated plates, RGD peptide coated plates, peptide-motif coated onto plates that constitute the active domains of fibronectin, collagen, laminin, and mixtures thereof.

In some embodiments, depending on the adherent substrate, the method further comprises isolating the population of pericytes expressing PDGFRβ, SM22, CD13 and Desmin to provide a pure population of pericytes (e.g. at least 95% pericyte).

Methods of isolating a cellular population based on cell surface markers (e.g., CD34− cell population, CD31− population, etc.) are known in the art and include, but are not limited to, for example, magnetic activated cell sorting (MACS), and fluorescence-activated cell sorting (FACS). Suitable agents for identifying cell surface markers are known in the art, for example, monoclonal antibodies specific to the cell surface marker. Suitably, the monoclonal antibodies may be fluorescently labeled themselves, or suitable secondary antibodies may be used depending on the method selected. For example, MACS method allows cells to be separated by incubating magnetic nanoparticles coated with antibodies against a particular surface marker to isolate cells that positively (+) and negatively (−) express the cell surface marker. For example, cells expressing the surface marker (e.g., CD31 or CD34) adhere to the magnetic nanoparticles and when run over a column in a magnetic field, the cells expressing the surface marker are retained in the column, and cells not expressing the surface marker (e.g., CD31− or CD34− cells) flow through and can be collected. FACS similarly incubates the cells with an antibody to a cell surface marker that is either directly conjugated to a fluorophore or uses a fluorescently labeled secondary antibody, and a specialized flow cytometer is use to separate the positively stained cells from the unstained cells.

Compositions of the first, second, and third chemically defined media are described herein. As used herein, the terms "chemically defined medium" and "chemically defined cultured medium" also refer to a culture medium containing formulations of fully disclosed or identifiable ingredients, the precise quantities of which are known or identifiable and can be controlled individually. As such, a culture medium is not chemically defined if (1) the chemical and structural identity of all medium ingredients is not known, (2) the medium contains unknown quantities of any ingredients, or (3) both. Standardizing culture conditions by using a chemically defined culture medium minimizes the potential for lot-to-lot or batch-to-batch variations in materials to which the cells are exposed during cell culture. Accordingly, the effects of various differentiation factors are more predictable when added to cells and tissues cultured under chemically defined conditions. As used herein, the term "serum-free" refers to cell culture materials that are free of serum obtained from animals (e.g., fetal bovine) blood. In general, culturing cells or tissues in the absence of animal-derived materials (i.e., under xenogen-free conditions) reduces or eliminates the potential for cross-species viral or prion transmission.

The chemically defined medium described herein includes a base medium and the specific added components recited. Base medium is a tissue culture medium which is able to allow for the culture and growth of cells under tissue culture conditions, such as E8 medium or DF3S medium, which are commercially available.

The first chemically defined medium, shown as E8BAC in Table 2, is E8 medium (Thermo Fisher Scientific, also known as Essential 8™ Medium, a xenogen-free and feeder-free medium specially formulated for the growth and expansion of human PSCs) supplemented with BMP4, Activin A and GSK-3 inhibitor (e.g., CHIR99021). The second chemically defined medium used in the methods herein, labeled as E7Vi in Table 2, is DF3 S medium (See, e.g., Zhang et al 2017 Stem Cell Reports, Schwartz et al 2016 PNAS for medium, which is incorporated by reference in its entirety) supplemented with transferrin, insulin, FGF2, VEGFA(165) and TGFβ1 inhibitor (e.g., SB431542). The third chemically defined medium used in the present invention is EGM-2 medium minus the antibiotic supplement (EGM-2, Promo-Cell #C-22111). The first two chemically defined media used are serum-free media. In one suitable embodiment, the first chemically defined medium is E8 medium supplemented with, comprising, consisting essentially of or consisting of 5 ng/ml BMP4, 25 ng/ml Activing A, and 1 µM of a GSK-3 inhibitor (e.g., CHIR99021). In one suitable embodiment, the second chemically defined medium is DF3S medium supplemented with, comprising, consisting essentially of or consisting of about 10-11 ng/ml transferrin, about 20 ng/ml insulin, about 100 ng/ml FGF2, about 50 ng/ml VEGF-A (165), and about 5 µM TGFβ1 inhibitor. EGM-2 medium is commercially available from PromoCell and Lonza.

The pluripotent stem cells used in the practice of the methods described herein may be any embryonic stem cells (ESCs), including ESC cell lines or induced pluripotent stem cells (iPSCs) including iPSC lines. Suitable ESCs and iPSCs are commercially available. Further, human ESCs can be obtained by methods known in the art. For example, human ESCs can be prepared from the inner cell mass (ICM) of blastocysts as described in, e.g., U.S. Pat. No. 5,843,780 to Thomson et al. or in Reubinoff et al. (Nature Biotech 18: 399, 2000). Alternatively, human ESCs may be obtained from commercial sources. Methods of obtaining iPSCs are known in the art and can be derived from numerous cell types. Methods of culturing and expanding ESCs and iPSCs are well known in the art.

The methods described herein provide advantages of known methods in (1) using simple, chemically defined medium containing only a few additional supplements, (2) the differentiation of cells in single monolayers without the use of feeder cells or embryoid bodies, and (3) provide a rapid method of differentiating pericytes, wherein a pure population of pericytes is obtained within 8-12 days in culture. The pericytes can be expanded in culture of at least 7-8 passages.

The methods described herein can provide in vitro derived pure population of 95% pericytes, preferably at least 98% pericytes where the pericytes express at least one pericyte marker (PDGFRβ, SM22, CD13 or Desmin) and preferably express all four pericyte markers PDGFRβ, SM22, CD13 and Desmin.

GSK-3 inhibitors used in the methods described herein are known in the art, and include, but are not limited to, CHIR990221, SB216763, CHIR-9014, TWS119, among others. Suitably, medium can be supplemented with about 1-5 µM GSK-3 inhibitor, alternatively from about 1-3 µM, preferably about 1 µM.

The concentration of bone morphogenic protein 4 (BMP4) used in the methods described herein is from about 1.0 ng/mL to about 30 ng/mL. In some embodiments, the concentration of BMP4 is from about 1 ng/mL to about 10 ng/mL. In a specific embodiment, the concentration of BMP4 is about 5 ng/mL.

The concentration of Activin A used in the first chemically defined medium (e.g., E8BAC) is about 10 to about 30 ng/ml, preferably about 20 to about 30 ng/ml. In a specific embodiment, the concentration of Activin A is about 25 ng/ml.

Suitable concentrations of transferrin, insulin, FGF2, VEGF-A(165), and the TGFβ1 inhibitor in the second chemically defined medium are sufficient to differentiate the cells into discrete CD34+/CD34− (CD31+/CD31−) cell populations. Suitable concentrations of transferrin are about 5-15 µg/ml transferrin, alternatively in some embodiments about 7-12 µg/ml. In a specific embodiment, the concentration of transferrin is 10.7 µg/ml. Suitable concentrations of insulin are about 10-30 µg/ml, alternatively in some embodiments about 15-25 µg/ml insulin. In a specific embodiment, the concentration of insulin is about 20 µg/ml. Suitable concentrations of FGF2 include about 70-150 ng/ml FGF2, alternatively in some embodiments about 75-125 ng/ml FGF2. In a specific embodiment, the concentration of FGF2 is about 100 ng/ml. Suitable concentrations of VEGF-A (165) include about 25-75 ng/ml, alternatively in some embodiments, about 40-60 ng/ml. In a specific embodiment, the concentration of VEGF-A(165) is 50 ng/ml. Suitable concentrations of TGFβ1 inhibitor include about 2-10 µM, alternatively in some embodiments, about 2-7 µM. In one specific embodiment, the concentration of TGFβ1 inhibitor is about 5 µM. TGFβ1 inhibitor are known in the art and include, but are not limited to, for example, SB431542, A83-01, Ki26894, LDN-193189, and Galunisertib (LY2157299). Suitable concentrations within these ranges are able to be determined by one of ordinary skill in the art.

The present invention also provides a population of exogenously derived pericytes from PSCs in vitro made by the method described herein. The population of exogenously derived pericytes in vitro are a pure population of pericytes (e.g. at least 95% pericytes) which express PDGFRβ, SM22, CD13 and Desmin. The pericytes of the present invention have different characteristics than primary pericytes derived from a subject as the in vitro derived pericytes have low expression of NG2, while primary pericytes have high expression of NG2, as demonstrated in FIG. 6. Further, the exogenously cultured pericyte population derived from PSCs are able to enwrap blood vessel endothelial cells to form blood vessels 3-D structure (see, e.g., FIG. 4).

In another embodiment, the present disclosure provides a method of isolating pericytes from CD34− or CD31− cell population, the method comprising culturing a substantially pure population of CD34− or CD31− cells derived from PSCs in EGM2 media for at least 2 days on an adherent substrate; detecting the pericyte markers PDGFRβ, SM22, CD13 and Desmin on a pericyte population of cells, wherein at least 95% of the cells are pericytes within the culture. In some embodiments, the method further comprises isolating the population of pericytes expressing PDGFRβ, SM22, CD13 and Desmin. In a preferred embodiment, the adherent substrate are plates coated with a mixture of collagen and fibronectin.

The pericytes differentiated by the methods described herein are early pericytes that are in an early unspecified state. The pericytes are identified by the expression of pericyte markers, particularly expression of PDGFRβ, SM22, CD13 and Desmin and which are CD31−/CD34− cells.

The exogenously cultured pericytes cultured by the methods described herein can be used for a number of different in vitro and in vivo applications, including tissue engineering, modeling of human disease, drug discovery and safety pharmacology. For example, the pericytes may be used in in vitro disease models or in vitro angiogenesis models. Further, cells may be used for drug discovery and new drug design. Additionally, the cells may be used in 3D tissue models and in screening toxicity of drugs or environmental chemicals. Further, the pericytes discussed herein may be used in in vitro 3D models of vasculature (production of vascularized 3D tissues), which can aid in the study and treatment of vascular diseases. Specifically, pericytes can be used to study defective endothelial-pericyte interactions in vitro for disease modeling and studies on tumor angiogenesis.

Another use of the pericytes of the present invention is the use in 3D and in in vitro cellular models that accurately reflect human physiology to improve the prediction of drug toxicity early in the development pipeline and would provide cost-effective approaches for testing other sources of chemical exposure, including food additives, cosmetics, pesticides, and industrial chemicals. For example, the pericytes may be used in a 3D neural construct that incorporate vascular and microglial components to develop neurotoxicity screening methods. The pericytes may be cultured with other brain components (e.g., neural progenitor cells, endothelial cells, mesenchymal stem cells and microglia/macrophage precursors) on synthetic hydrogels under defined conditions (see, e.g., Schwartz et al. 2016, Human pluripotent stem cell-derived neural constructs for predicting neural toxicity, PNAS, v.112, no. 40, pp. 12516-12521, incorporated by reference in its entirety) for testing of compounds.

For example, pericytes derived from a PSC cell line with MeCP2 mutation may be used to provide an in vitro model for studying Rett Syndrome.

Further, differentiated pericytes may be used in treatment of ischemic injuries like myocardial infarction, congestive heart failure, stroke, and peripheral vascular disorders in which there is damage to the blood vessels of a subject. Additionally, differentiated pericytes may be used for treatment of Rett Syndrome by administering wildtype-derived pericytes to counter the MeCP2 mutated pericytes within a subject having Rett Syndrome.

The current disclosure also provides kits for differentiating a pure population of pericytes in in vitro culture.

Aspects of the present disclosure that are described with respect to methods can be utilized in the context of the compositions of matter or kits discussed in this disclosure. Similarly, aspects of the present disclosure that are described with respect to compositions of matter can be utilized in the context of the methods and kits, and aspects of the present disclosure that are described with respect to kits can be utilized in the context of the methods and compositions of matter.

The above description, attached figures, and claims listed below are intended to be illustrative and not limiting of this invention. In light of the invention described herein, many themes and variations to this invention will be suggested to one skilled in the art. All such themes and variations are within the contemplation hereof. For instance, while this invention has been described in conjunction with the various exemplary embodiments outlined above and in the below claims, various alternatives, modifications, variations, improvements, and/or substantial equivalents, whether known or that are rare or may be presently unforeseen, may become apparent to those having at least ordinary skill in the art. Various changes may be made without departing from the spirit and scope of the invention. Therefore, the invention is intended to embrace all known or later-developed alternatives, modifications, variations, improvements, and/ or substantial equivalents of these exemplary embodiments.

It is to be understood that the invention is not limited to the particular embodiments described. It is also to be understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. In places where ranges of values are given, this disclosure explicitly contemplates other combinations of the lower and upper limits of those ranges that are not explicitly recited. For example, recitation of a value between 1 and 10 or between 2 and 9 also contemplates a value between 1 and 9 or between 2 and 10. Ranges identified as being "between" two values are inclusive of the end-point values. For example, recitation of a value between 1 and 10 includes the values 1 and 10.

The term "consisting essentially of" and "consisting of" should be interpreted in line with the MPEP and relevant Federal Circuit interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim. For example, with regard to sequences "consisting of" refers to the sequence listed in the SEQ ID NO. and does refer to larger sequences that may contain the SEQ ID as a portion thereof.

The present invention has been described in terms of one or more preferred embodiments, and it should be appreciated that many equivalents, alternatives, variations, and modifications, aside from those expressly stated, are possible and within the scope of the invention.

The invention will be more fully understood upon consideration of the following non-limiting examples.

EXAMPLES

Example 1: In Vitro Differentiation of Pericytes from Pluripotent Stem Cells

As depicted in FIG. 1A, one embodiment of the method of differentiating pericytes from PSCs is provided. Specifically, the method comprises the following steps:

A. Day −2. Pass the PSC cells using versene (Life technologies #15040-066) so that on Day 0 the cells will be 50% to 60% confluent (generally 1 in 3 split). Plate onto Matrigel™ coated wells of a 6 well plate in E8 media (Thermo Fisher #A1517001).
B. Day −1. Feed the cells with E8 media.
C. Day 0. Pass the PSC cells using versene so that the cells remain in small colonies and are not singular. Plate onto Matrigel coated wells of 6 well plates in 2 ml per well of E8BAC media with the addition of 10 µM Y27632 (R&D systems #1254/10). The cells should be plated such that on Day 2 the wells will be 100% confluent.
D. Day 1. Feed the cells with E8BAC media (without 10 µM Y27632)—2 ml per well.
E. Day 2. The cells should be 100% confluent. Feed the cells with E7Vi media 44 hours after plating on Day 0.
F. Day 3. Feed the cells with 3 ml per well of E7Vi media.
G. Day 4. Feed the cells with 4 ml per well of E7Vi media.
H. Day 5. Feed the cells with 5 ml per well of E7Vi media.
I. Day 6. Harvest the cells using Accutase to produce a single cell suspension, count and resuspend $75 \times 10^6$ cells in 300 µl of cold MACS buffer (PBS+0.5% BSA+2 mM EDTA). Add 100 µl of FcR blocking reagent and 100 µl of CD34 microbeads (Miltenyi Biotec #130-046-702), mix well and incubate at 4° C. for 30 mins.
J. Wash the cells with 10 ml MACS buffer and pellet by centrifugation; resuspend pelleted cells in 500 µl of MACS buffer.
K. Place an LS column (Miltenyi Biotec #130-042-401) on a magnet holder and wash the column with 3 ml MACS buffer.
L. Apply the cell suspension to the column and collect the unbound CD34− cells from the flow through.
M. Wash the column with 9 ml of MACS buffer and collect the flow through containing the CD34− cells.
N. Count the CD34− pericytes precursors cells and plate to 6 well plates pre-coated with 0.25 µg/cm² of a 1:1 mixture of Fibronectin (Corning #356008) and Collagen IV (Corning #354245). Plate the cells in EGM-2 (do not include the antibiotic bullet component GA-1000 in the medium, PromoCell #C-22111) with $2 \times 10^4$ cells per cm².

TABLE 1 culture conditions

| Culture plate | Media (ml) | Fibronectin (µl) from 1 mg/ml stock | Collagen (µl) from 3.35 mg/ml stock |
|---|---|---|---|
| T75 flask | 10 | 18.75 | 5.6 |
| 6 well plate | 12 (2 ml per well) | 14.4 | 4.3 |

O. Feed the cells daily with EGM-2 and pass when the cells are around 80% to 90% confluent which takes 1 to 3 days of culture.
P. Pass the cells using TrypLE (Life technologies #12563-029), plate (generally 1 in 3 split) to T75 flasks pre-coated with 0.25 μg/cm² of a 1:1 mixture of Fibronectin and Collagen IV. Plate cells in PM complete media without adding the antibiotic supplement (P/S, ScienCell #1201, #1252).

Q. QC the cells using flow cytometry using antibodies for CD13-PE (BD cat #555394), CD140b-PE (BD cat #558821) and CD34-APC (BD cat #555824). The cells should be CD13 and CD140b positive and CD34 negative.

R. Freeze the cells when around 80% confluent (which takes 3 to 5 days of culture) with 2×10⁶ cells per vial in 40% PM complete media, 50% FBS and 10% DMSO.

TABLE 2 chemically defined medium.

| Media Name | Base Medium | Components | Component Catalogue Numbers | Working Conc. | Stock Conc. | Dilution |
|---|---|---|---|---|---|---|
| E8BAC | E8 | BMP4 | R&D Systems #314-BP-010/CF | 5 ng/ml | 100 μg/ml | 20000 |
| | | Activin A | R&D Systems #338-AC-50/CF | 25 ng/ml | 100 μg/ml | 4000 |
| | | CHIR 99021 | R&D Systems #4423 | 1 μM | 10 mM | 10000 |
| E7Vi | DF3S Gibco A1453 5DJ | SB341542 | R&D systems #1614 | 5 μM | 10 nM | 2000 |
| | | VEGFA165 | R&D systems #293-VE-500/CF | 50 ng/ml | 100 μg/ml | 2000 |
| | | FGF2 | | 100 ng/ml | 100 μg/ml | 1000 |
| | | Transferrin | R&D systems #2914-HT | 10.7 μg/ml | 10.7 mg/ml | 1000 |
| | | Insulin | Sigma I9278 | 20 μg/ml | 10 mg/ml | 500 |

Example 2: Chemically Defined Protocol for Pericyte Differentiation of Induced Pluripotent Stem Cell Lines The following example builds on Example 1 demonstrating the differentiation of pericytes from iPSCs derived from wildtype (WT83), MeCP2 duplicate (M2), MeCP2 mutation (Q83X) and a well-established iPSC line (WTC11, wildtype) using the novel differentiation procedure of the present invention. iPSCs were differentiated in defined media with minimal media supplementation in monolayer culture and a reduced differentiation timeline. The purity of differentiated pericyte populations was assessed by flow cytometry and immunofluorescence, while the function of the pericytes between different cell lines was investigated through an angiogenesis assay.

Pericytes play a key role in vascular development and function. They are multi-faceted and work to stabilize the vasculature and vascular permeability through matrix synthesis, regulate blood flow and angiogenesis, participate in repair, and in some cases, serve as progenitor cells of mesenchymal and macrophage lineages[1-4]. Due to their prominence in regulating vasculature, pericytes have been found throughout the body, with the highest density found in the brain[5]. In the central nervous system, the ratio of pericytes to endothelial cells is 1:1, forming the blood-brain barrier in order to filter out any potentially toxic blood-derived factors[6].

In recent years, pericytes have been found to be particularly important in a variety of diseases. For instance, diabetic retinopathy is linked to the selective loss of pericytes[7]. This dropout of pericytes results in morphological alterations in microvessels, increased vascular permeability, and eventually hyperglycemia and local hypertensionm[7]. Initial studies investigating the use of pericyte progenitor cells in diabetic retinopathy rat models have shown successful pericyte regeneration[8]. Additionally, pericytes have been found to be critical to the metastasis and spread of multiple types of cancer[9-11]. Abnormalities in the number and coverage of pericytes has been correlated to cancer prognosis in a number of clinical trials. Increased pericyte coverage on tumor microvessels is indicative of resistance to therapy and unfavorable clinical outcomes[12, 13], whereas, pericyte reduction or dysfunction leads to increased vessel permeability, favoring tumor cell invasion and increased metastasis[14]. While these studies indicate the importance of pericytes in pathology, our current understanding of the role pericytes play in other diseases remains to be limited.

Rett syndrome is one of the most common causes of intellectual disability among females and is highly prevalent, occurring in 1 of 10000 live female births[15]. The neurological disorder is caused by mutation of the methyl CpG-binding protein (MeCP2) gene[16] and is characterized by autistic features, seizures, developmental delay and loss of motor skills and speech[17]. MeCP2 is an X-linked epigenetic transcriptional regulator that is abundant in a variety of cell types and tissues including neurons and endothelial cells[18-20]. In addition to the prominent neurological symptoms, patients with Rett syndrome often have hypo-perfusion of varying severity in the midbrain and upper brainstem, as well as poor circulation[21,22]. The neurological Rett phenotype has been recapitulated in both animal models as well as human neurons [19,23,24], however, the effect of MeCP2 mutation on human pericytes and neurovascular development have yet to be elucidated.

Recent advances in human induced pluripotent stem cell (iPSC) technologies have made it possible to generate various types of vascular cells including endothelial cells and pericytes in vitro in order to study vascular biology and diseases. Although multiple independent laboratories have published protocols for pericyte differentiation[25], the protocols are often difficult to reproduce due to non-standardized or complicated media formulations requiring extensive media supplementation[26], the formation of aggregates or embryoid bodies[27, 28], and long differentiation times[29].

This often results in low efficiencies and purities and variations in differentiation from batch-to-batch. The goal of this study was to demonstrate the differentiation of pericytes from iPSCs derived from wildtype (WT83), MeCP2 duplicate (M2), MeCP2 mutation (Q83X) and a well-established iPSC line (WTC11) using a novel differentiation procedure. iPSCs were differentiated in defined media with minimal media supplementation in monolayer culture and a reduced differentiation timeline. The purity of differentiated pericyte populations was assessed by flow cytometry and immunofluorescence, while the function of the pericytes between different cell lines was investigated through an angiogenesis assay.

Results

ECs and PCs were derived from induced pluripotent stem cells (iPSCs) from WTC11, MeCP2 wildtype (WT83), MeCP2 duplicate (M2), and MeCP2 mutation (Q83X) cell lines following a chemically defined, monolayer differentiation procedure (FIG. 1A). Representative brightfield images show the morphological changes of the stem cell procession into the mesoderm intermediate step and further differentiation into two major distinct cell populations of presumably endothelial progenitor cells and pericyte progenitor cells (FIG. 1B) (demonstrated by flat large cells in roughly circular area are presumptive endothelial progenitor cells and the smaller, denser cells surrounding the areas of large flat cells are the presumptive pericytes). At day 6 of differentiation, the EC and PC progenitor populations are sorted using CD34 immunomagnetic beads, with the CD34− cell population consisting of the PC progenitor cells and the CD34+ cell population consisting of the EC progenitor cells, respectively.

Figure 2:
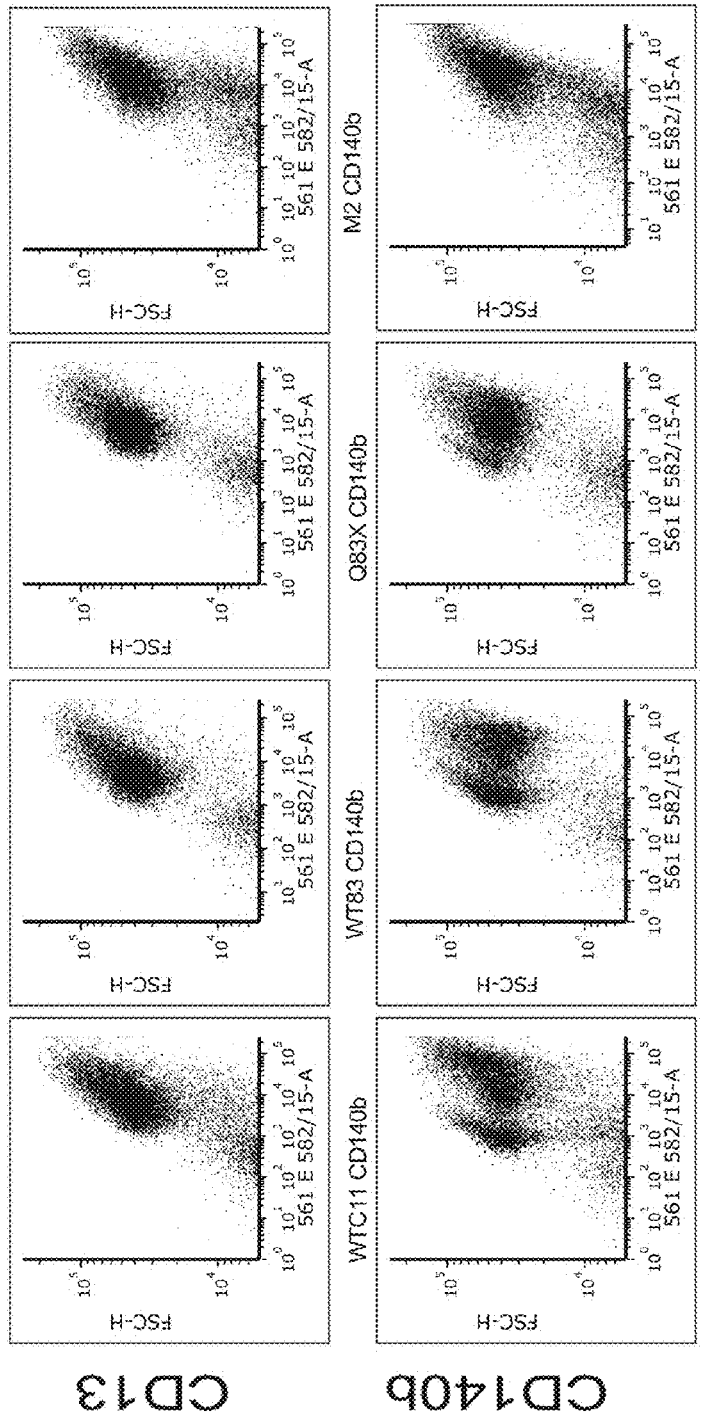
FIG. 2. Flow cytometry (A) of pericytes derived from WTC11, WT83, Q83X, and M2 iPSC cell lines for the pericyte markers CD13 and CD140b (anti-PDGFRβ) with (B) corresponding positive percentages.

After cell selection and further expansion in pericyte media on collagen:fibronectin-coated plates, the purity of the pericyte population was determined by flow cytometry for the pericyte specific markers CD13 and CD140b (anti-PDGFRβ) (FIG. 2A). The differentiation and separation procedure resulted in high yield and high purity (greater than 95%) for all cell types: WTC11 PCs were 97.1% CD13+ and 95.5% CD140b+, WT83 PCs were 99.8% CD13+ and 99.3% CD140b positive, Q83X PCs were 99.9% CD13+ and 99.9% CD140b+ and M2 were 97.1% CD13+ and 95.2% CD140b+(FIG. 2B). Pericytes also stained positive for Desmin, another pericyte marker.

Figure 3:
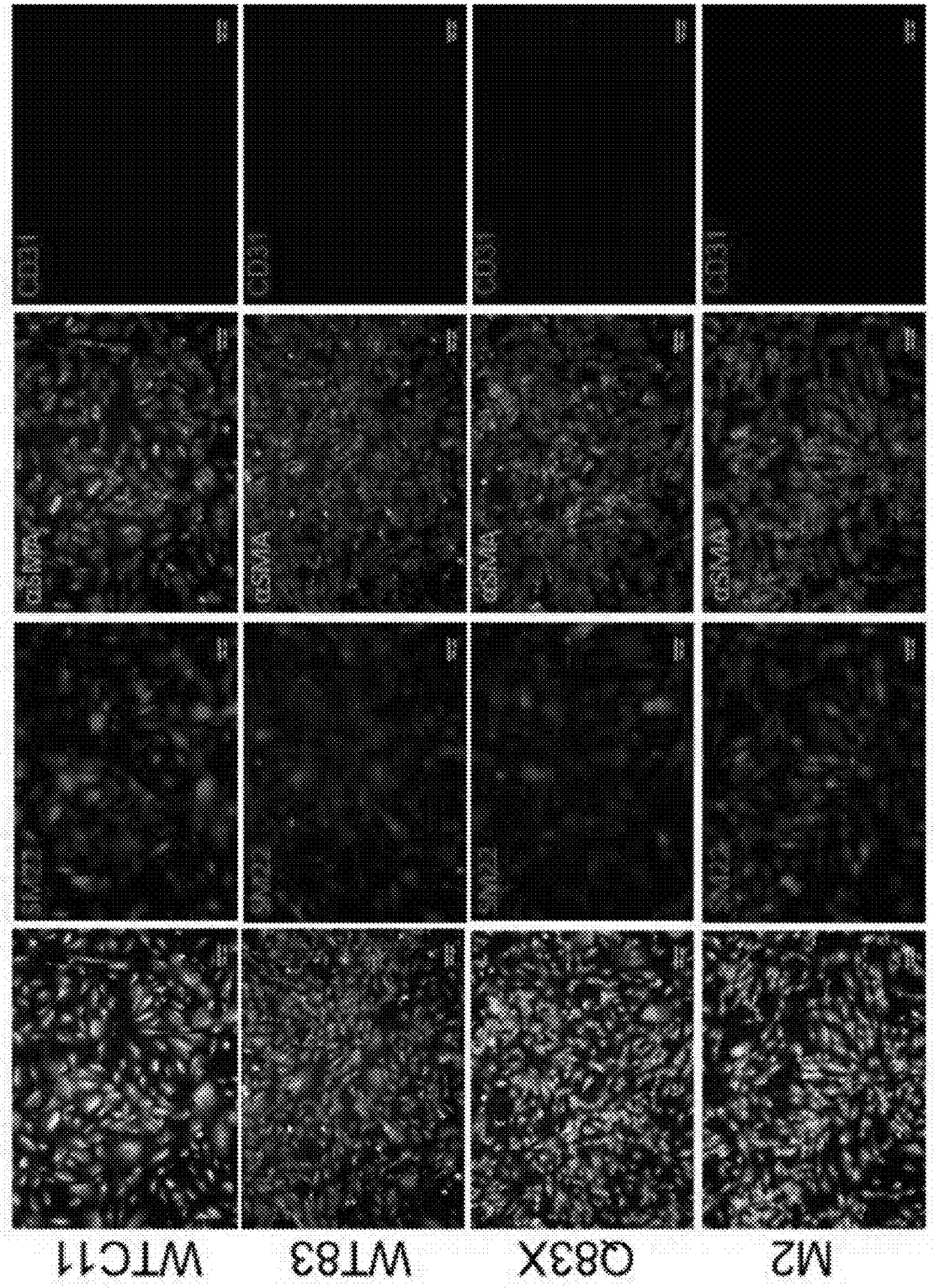
FIG. 3. Representative immunofluorescent images of iPSC-derived pericytes. Representative immunofluorescent images of iPSC-derived pericytes stained for the pericyte markers SM22 (red) and αSMA (green), the endothelial marker CD31 (pink), and nuclei counterstained with DAPI (blue) from WTC11, WT83, Q83X and M2 iPSC cell lines (scale bar=100 μm). The first image in each row is a merge of all the color channels for that image, showing coincidental detection (or lack thereof) of all pericyte specific markers and DAPI.

Immunofluorescent staining for pericyte specific markers revealed the expression of the smooth muscle markers smooth muscle-specific protein 22 (SM22) and alpha-smooth muscle actin (α-SMA) of the pericytes differentiated from WTC11, WT83, Q83X, and M2 iPSC lines (FIG. 3). A high level of expression of SM22 and α-SMA was found in all cell populations, with a majority of cells co-expressing the two pericyte markers. Co-localization and morphology were not investigated in this study; however, there were no apparent dissimilarities among the different cell lines. CD31, a marker of endothelial cells, was not expressed by the cells. This indicates that the isolation of pericytes from ECs with the immunomagnetic beads was effective and that after further expansion of the PC progenitors, the pericytes maintain their phenotype and do not express markers of endothelial cells.

Figure 4:
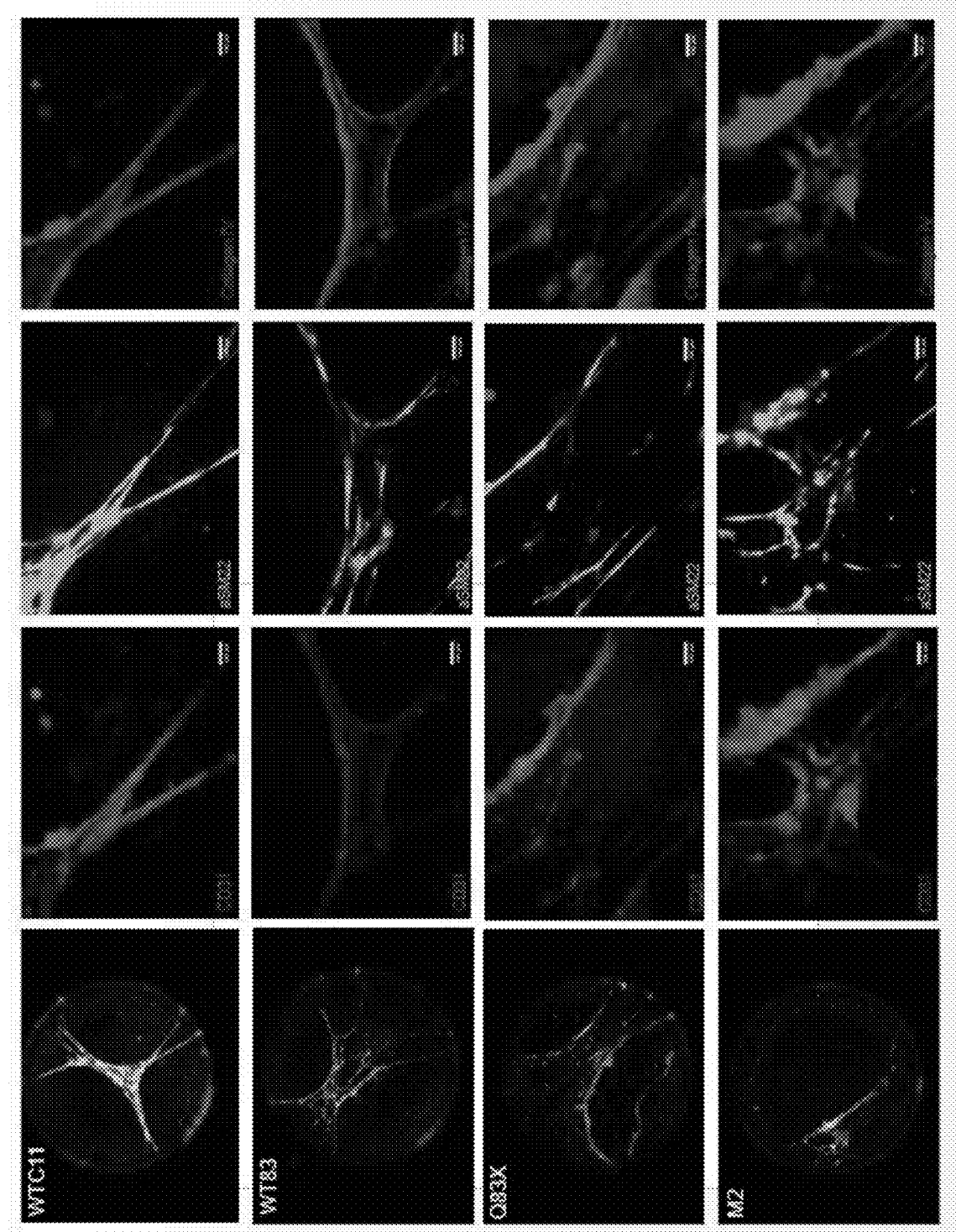
FIG. 4. Representative immunofluorescent images of an angiogenesis assay of iPSC-derived ECs and PCs from the different cell lines and stained for the endothelial marker CD31 (pink), the pericyte marker SM22 (green), and collagen IV (red) matrix deposited by the pericytes at day 5 (scale bar=100 μm). The first image in each row is a merge of all the color channels for that image, showing coincidental detection (or lack thereof) of all pericyte specific markers and DAPI.
Figure 5:
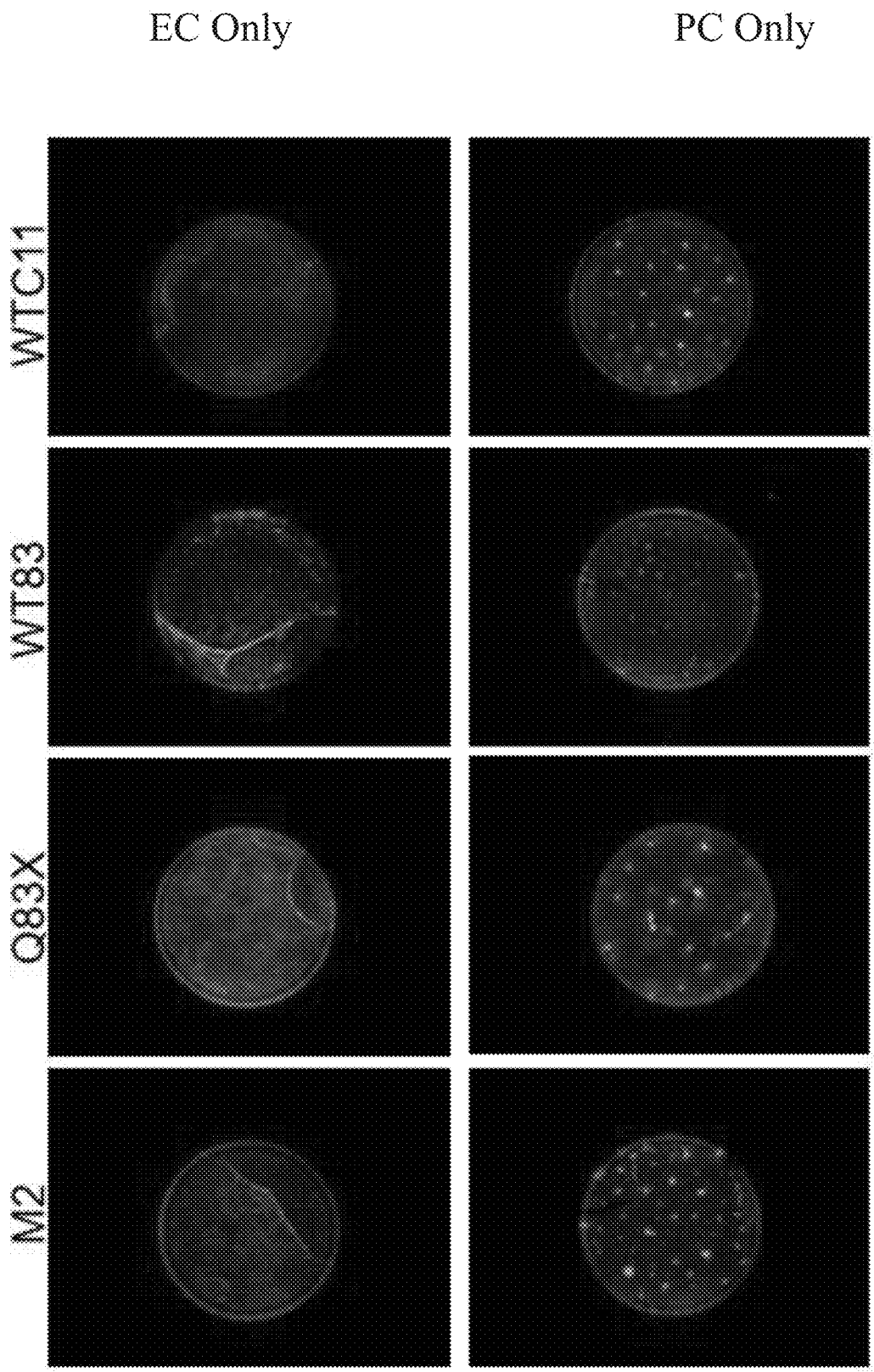
FIG. 5. Representative color channel merged images of an angiogenesis assay of iPSC-derived ECs-only and PCs-only from WTC11, WT83, Q83X and M2 iPSC cell lines and stained for the endothelial marker CD31 (pink), the pericyte marker SM22 (green), collagen IV (red) matrix deposited by the pericytes, and nuclei counterstained with DAPI (blue) at day 5.

The functionality of pericytes was examined with an angiogenesis assay in which ECs and PCs, derived from the same cell line, were co-cultured and the formation of a vascular network was assessed by immunofluorescence (FIG. 4). After 5 days, all cell lines show positive expression of ECs (CD31), pericytes (SM22) and matrix deposition (collagen IV). WTC11 derived ECs and pericytes developed a highly branched, tubule network. Representative images show ECs and PCs aligned and higher intensity of collagen IV on the outside of the tubules. WT83 ECs and PCs also resulted in a highly branched network with similar alignment and matrix deposition as the WTC11 cell population. The MeCP2 mutation line, Q83X, appeared to form one large tubule, but was not as branched as the previously discussed populations. The MeCP2 duplicate line, M2, also formed tubules after 5 days. While the cells appear to branch more than the Q83X ECs and PCs, it does not span across the well, and branching does not appear to be bifurcating as is the case with the WTC11 and WT83 populations. ECs-alone and PCs-alone from any cell line did not result in tubule formation (FIG. 5). The same number of ECs and PCs were added in all wells across all four parental cell lines assayed.

Figure 6:
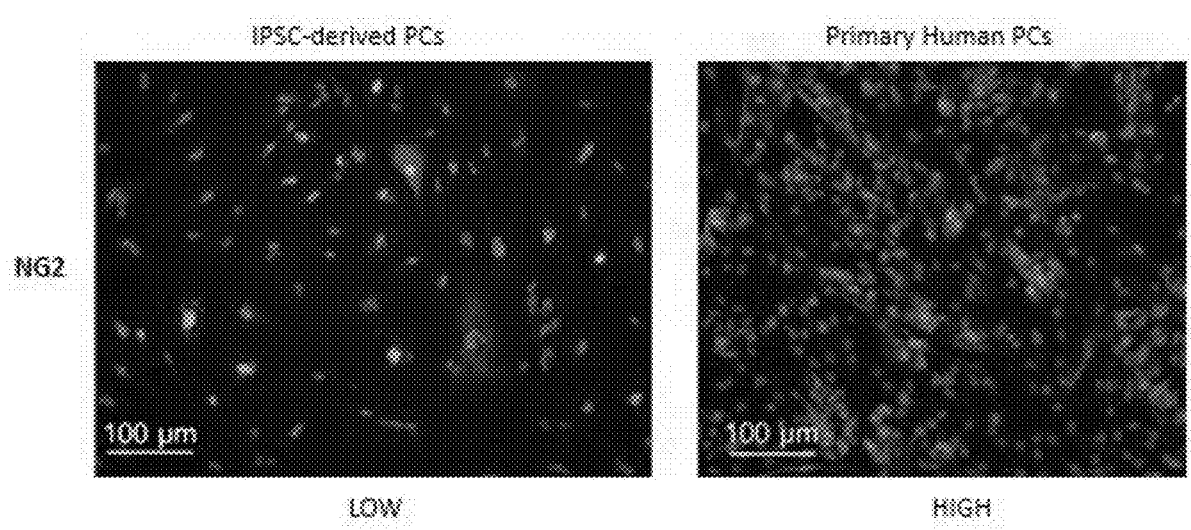
FIG. 6. Representative merge images of the differences in PC specific marker detection between iPSC-derived PCs and primary human PCs.

Further, primary human pericytes were purchased from ScienCell and stained as described. FIG. 6 contains representative figures showing the staining of iPSC-derived PCs and primary Human PCs. As demonstrated, the in vitro differentiated pericytes do not express NG2 as it is expressed in primary human PCs.

Discussion

Pericytes are a critical component of the neurovascular unit, making them an ideal cell type for disease modeling, drug screening, and cell-based therapies[30-32]. The chemically-defined, monolayer differentiation protocol described herein resulted in successful differentiation of pericytes from iPSCs of four cell lines: WTC11, wildtype WT83, MeCP2 duplicate (M2), and MeCP2 mutation (Q83X). The protocol also results in the differentiation of an endothelial progenitor cell population. High purity pericyte populations and pericyte-specific protein expression were achieved for all cell lines as demonstrated by flow cytometry and immunofluorescence. Pericyte function, as determined by an angiogenesis assay, suggests that the angiogenic capabilities of the pericytes may be cell-line specific and may recapitulate differences in vascularity observed in patients with MeCP2 mutations. These MeCP2 pericytes may be used for an in vitro model for the study of Rett Syndrome.

Given the potential of iPS-derived cells for therapies and human disease modeling, differentiation protocols that are highly reproducible, ubiquitous for multiple cell lines, chemically defined, and have short differentiation timelines are necessary. While pericyte differentiation from embryoid bodies has shown some success[27,28], embryoid bodies often lack homogeneity of cell exposure to environmental factors due to limited mass transfer and are not easily amenable to scale-up[33,34]. The monolayer culture described in this study eliminates these disadvantages by removing the necessity of aggregate formation. The differentiation of pericytes from iPSCs in a monolayer environment has been previously described; however, the protocol requires nearly a month of cell expansion and differentiation until a pure, functional pericyte population is achieved[29]. Alternatively, the protocol developed in this study produced pericyte progenitor cells on the order of six days, ultimately reducing the time by approximately 2-3 fold. The ability to differentiate multiple cell lines, including cell lines from individuals with neuronal diseases and atypical neural development, also makes this protocol advantageous, as previous studies have only reported pericyte differentiation of a single line.

Pericytes are often indistinguishable from smooth muscle cells or a differentiated subpopulation of mesenchymal stem cells, making validation of their differentiation difficult [35-38]. However, recent studies have found pericyte markers that are specific to the brain and neurovascular space. CD140b (anti-PDGFRβ) and CD13 are classic brain pericyte markers[39,40]. CD140b plays a pivotal role in vascular stability and integrity during brain development as it binds to endothelial cells of newly formed blood vessels[5]. Mice lacking CD140b completely lack brain pericytes, resulting in abnormal vasculature and blood brain barrier[41, 42]. In addition, CD13 labeled pericytes have been found in the brain cortex and ventricular-subventricular zone in adult mice brains, and also co-express CD140b[43]. CD13 and CD140b have also been found not to co-label CD31+ endothelial cells[43], making them effective markers to distinguish pericytes from other vascular cells and validate the differentiation of pericytes in this study.

An interesting finding from this study suggests that M2 and Q83X-derived pericytes may have reduced angiogenic capabilities. The primary function of pericytes in vivo is to deposit extracellular matrix proteins, specifically collagen IV, which makes up the majority of the basement membrane of the brain in order to help stabilize the vasculature[44]. Results from this study found that pericytes derived from M2 and Q83X cell lines showed reduced tubule formation and collagen IV deposition compared to the wildtype cell lines. It is postulated that the pericytes derived from the MeCP2 mutation and MeCP2 duplicate cell lines may recapitulate similar function to what is found in vivo, where in a clinical study 11 out of 13 Rett patients had hypoperfusion of ranging severity[21]. A Not to be bound by any theory, but a potential mechanism for the decreased blood flow seen in vivo may be due to decreased angiogenic capabilities of MeCP2 mutated pericytes seen in vitro.

In conclusion, this study presents a differentiation protocol that can be used to derive pericytes from iPSCs from multiple cell lines, which in turn can be applied to many applications such as cell based therapies, disease modeling and toxicity/therapeutic screening. Future work will incorporate iPSC-derived pericytes in neural organoids to investigate vascularity in a human brain model.

Experimental Procedures

Cell Maintenance for Differentiation

Human induced pluripotent stem cells (iPSCs) were initially thawed in Essential 8 (E8) medium (Gibco) with 10 µM Rock Inhibitor Y27632 for 24 hours on Matrigel (Corning)-coated tissue culture plates, after which, cells were maintained in E8 media until cells reached approximately 50% confluence. To initiate differentiation (Day 0), iPSCs were passaged using Versene (Gibco) (7 minutes, 37° C.) and split at a 1:2 ratio onto a Matrigel coated 6 well tissue culture plate in E8BAC+Y medium (E8 media, 5 ng ml$^{-1}$ BMP4, 25 ng ml$^{-1}$ Activin A, 1 µM CHIR 99021, 10 µM Rock Inhibitor Y27632); the medium was changed at 24 hours to E8BAC medium (E8 media, 5 ng ml$^{-1}$ BMP4, 25 ng ml$^{-1}$ Activin A, 1 µM CHIR 99021). At 44 hours, the cells were 100% confluent and the media was changed to E7Vi (DF3S (Gibco), 5 uM SB341542, 50 ng ml$^{-1}$ VEGFA165, 100 ng ml$^{-1}$ FGF2, 10.7 µg ml$^{-1}$ transferrin, 20 µg ml$^{-1}$ insulin). For the following 3 days, E7Vi media was replaced every day; as needed the volume per well was increased as the cell density and metabolism of the cells increased.

CD34 Magnetic-Activated Cell Sorting (MACS)

At day 6, cells were dissociated with Accutase, centrifuged, and resuspended at $7.5 \times 10^7$ cells total (live and dead) in 300 µL of cold MACS buffer (PBS+0.5% BSA+2 mM EDTA). 100 µl of FcR blocking reagent and 100 µl of CD34 magnetic microbeads (Mitenyi Biotec) were added to the cell suspension. The solution was mixed well and incubated at 4° C. for 30 minutes. Cells were then washed with 10 mL MACS buffer and centrifuged at 300×g for 10 minutes. The supernatant was completely removed, cells and beads were resuspended in 500 µL MACs buffer, and placed on ice until magnetic separation. The LS column was placed on the magnet and was washed carefully with 3 mL MACS buffer to avoid bubbles. The cell suspension was added to the column, and the unbound CD34− cells were collected in the flow-through. The original cell suspension tube was washed with 500 µL MACS to remove any residual cells, and was added to the column. The column was washed with an additional 9 mL of MACS buffer. The collected cells were placed on ice. The column was removed from the magnet, 5 mL MACS buffer was added, and the column plunger was slowly pushed to flush out the attached CD34+ cells. An additional 5 mL of buffer was added to the column and plunged through to remove any residual CD34+ cells. The CD34+ cells (endothelial cells) were either banked for future experiments or continued in culture.

Differentiating CD34− Pericyte Precursors

The CD34− cells were plated onto a 1:1 fibronectin:collagen (1.2 µg ml$^{-1}$ fibronectin, 1.2 µg ml$^{-1}$ collagen I in DMEM/F12 (Gibco)) coated tissue culture dish at $2 \times 10^4$ cells cm$^{-2}$ in Endothelial Cell Growth media (EGM2, PromoCell) and the media was changed after 24 hours. At 48 hours (Day 8), the pericyte precursor cells (90% confluent) were dissociated with TrypLE for 5 minutes, and plated on 1:1 fibronectin:collagen coated tissue plastic in PM media.

Flow Cytometry

Pericytes were detached from the fibronectin:collagen coated tissue culture plates using TrypLE for 5 minutes at 37 C. The TrypLE was deactivated with 2× volume of FACS buffer (2% FBS in PBS). The cells were centrifuged for 5 minutes at 300 g and resuspended to ensure 500,000 cells per tube. The cells were incubated with primary antibodies conjugated to fluorophores (CD13-PE (BD Biosciences, BD555394), CD140b-PE (BD Biosciences, BD558821), and CD34-APC (BD Biosciences, BD55824)) at room temperature for 30 minutes. The cells were washed, centrifuged, and resuspended in FACS buffer, and flow cytometry was run using an LSRII Flow Cytometer (BD Biosciences).

Immunofluorescence Characterization

The CD34− pericytes from the different cell lines (WT83 Passage 3 Day 8, WTC11 Passage 4 Day 16, Q83X Passage 3 Day 8, M2 Passage 4 Day 16) were plated onto 1:1 fibronectin:collagen coated plates and cultured for 24 hours in Pericyte Medium minus the antibiotic supplement (PM, ScienCell Research Laboratories). At 24 hours, the cells were fixed with 4% PFA for 1 hour at room temperature, then washed with PBS. Cells were blocked with 10% normal donkey serum (NDS) 1% BSA 0.25% Triton X in PBS for 1 hour at room temperature. Primary antibodies were diluted in 1% NDS 1% BSA 0.25% Triton-X in PBS and applied as follows: 1:200 mouse anti-αSMA (Cell Signaling, 48938), 1:200 rabbit anti-SM22a (Thermo Fisher, PA5-27463), 1:250 hamster anti-CD31 (Abcam, ab119341) and incubated overnight at 4° C. Cells were washed 3 times with PBS; secondary antibodies (Anti-mouse AlexaFluor 488, anti-rabbit AlexaFluor 468, anti-hamster AlexaFluor 647) were diluted at 1:200 in 1% NDS 1% BSA in PBS, applied, and incubated in the dark for 1.5 hours at room temperature.

Nuclei were counterstained with DAPI (5 ug/ml) for the last 15 minutes of incubation. Cells were then washed with PBS and stored at 4° C. until imaged at 10× magnification using a Nikon Eclipse-Ti microscope.

Angiogenesis Assay

ECs ($1.5 \times 10^4$) and PCs ($3 \times 10^3$) differentiated from the same cell line were added to each well of a Geltrex-Matrigel (Gibco) coated angiogenesis plate (Ibidi) and cultured in E7V media at standard culture conditions (5% $CO_2$, 37° C.). Cells were fixed with 4% paraformaldehyde for 30 minutes at room temperature at 24 hours and 5 days. After fixation, cells were washed with PBS and blocked with 10% NDS, 1% BSA, and 0.25% Triton X in PBS for 2 hours at room temperature, and stained with primary antibodies for CD31 (Abcam, ab119341) and PDGFRβ (Cell Signaling, 3169) in 1% NDS, 1% BSA, 0.25% Triton X in PBS overnight at 4° C. Cells were washed three times in PBS, and fluorescence-conjugated secondary antibodies were applied in the dark at room temperature for 1.5 hours. The fixed cells were imaged at 4× and 10× magnification using a Nikon Eclipse-Ti Microscope.

REFERENCES FOR EXAMPLE 2

[1] M. Hellström, H. Gerhardt, M. Kalén, X. Li, U. Eriksson, H. Wolburg, C. Betsholtz, *J. Cell Biol.* 2001, 153, 543.
[2] T. L. Pallone, E. P. Silldorff, *Exp. Nephrol.* 2001, 9, 165.
[3] M. Enge, M. Bjarnegård, H. Gerhardt, E. Gustafsson, M. Kalen, N. Asker, H.-P. Hammes, M. Shani, R. Fässler, C. Betsholtz, *EMBO J.* 2002, 21, 4307.
[4] W. E. Thomas, *Brain Res. Brain Res. Rev.* 1999, 31, 42.
[5] G. Bergers, S. Song, *Neuro-Oncol.* 2005, 7, 452.
[6] D. Shepro, N. M. Morel, *FASEB J.* 1993, 7, 1031.
[7] E. B. and M. Porta, "Pericyte Loss in Diabetic Retinopathy: Mechanisms and Consequences," can be found under http://www.eurekaselect.com/113178/article, 2013.
[8] J. M. Kim, K.-S. Hong, W. K. Song, D. Bae, I.-K. Hwang, J. S. Kim, H.-M. Chung, *Stem Cells Transl. Med.* 2016, 5, 1268.
[9] Z. Chen, X. H. Xu, J. Hu, *Neoplasma* 2016, 63, 173.
[10] A. E. Paiva, L. Lousado, D. A. P. Guerra, P. O. Azevedo, I. F. G. Sena, J. P. Andreotti, G. S. P. Santos, R. Gonçalves, A. Mintz, A. Birbrair, *Cancer Res.* 2018, DOI 10.1158/0008-5472.CAN-17-3883.
[11] H. Gerhardt, H. Semb, *J. Mol. Med.* 2008, 86, 135.
[12] G. Bergers, D. Hanahan, *Nat. Rev. Cancer* 2008, 8, 592.
[13] J. R. van Beijnum, P. Nowak-Sliwinska, E. J. M. Huijbers, V. L. Thijssen, A. W. Griffioen, *Pharmacol. Rev.* 2015, 67, 441.
[14] X. Xian, J. Håkansson, A. Ståhlberg, P. Lindblom, C. Betsholtz, H. Gerhardt, H. Semb, *J. Clin. Invest.* 2006, 116, 642.
[15] C. L. Laurvick, N. de Klerk, C. Bower, J. Christodoulou, D. Ravine, C. Ellaway, S. Williamson, H. Leonard, *J. Pediatr.* 2006, 148, 347.
[16] J. L. Neul, P. Fang, J. Barrish, J. Lane, E. B. Caeg, E. O. Smith, H. Zoghbi, A. Percy, D. G. Glaze, *Neurology* 2008, 70, 1313.
[17] E. E. J. Smeets, K. Pelc, B. Dan, *Mol. Syndromol.* 2012, 2, 113.
[18] I. M. Caballero, B. Hendrich, *Hum. Mol. Genet.* 2005, 14 Spec No 1, R19.
[19] A. Panighini, E. Duranti, F. Santini, M. Maffei, T. Pizzorusso, N. Funel, S. Taddei, N. Bernardini, C. Ippolito, A. Virdis, et al., *PLoS ONE* 2013, 8, DOI 10.1371/journal.pone.0064863.
[20] C. Wang, F. Wang, Z. Li, Q. Cao, L. Huang, S. Chen, *Stem Cell Res. Ther.* 2018, 9, DOI 10.1186/s13287-018-0828-y.
[21] R. Lappalainen, K. Liewendahl, K. Sainio, P. Nikkinen, R. S. Riikonen, *Acta Neurol. Scand.* 1997, 95, 44.
[22] G. Bianciardi, M. Acampa, I. Lamberti, S. Sartini, M. Servi, F. Biagi, V. Bocchi, J. Hayek, M. Pastorelli, *Clin. Hemorheol. Microcirc.* 2013, 54, 109.
[23] L. Ricceri, B. De Filippis, G. Laviola, *Behav. Pharmacol.* 2008, 19, 501.
[24] J. Guy, J. Gan, J. Selfridge, S. Cobb, A. Bird, *Science* 2007, 315, 1143.
[25] J. Xu, T. Gong, B. C. Heng, C. F. Zhang, *FASEB J.* 2017, 31, 1775.
[26] Orlova Valeria V., Drabsch Yvette, Freund Christian, Petrus-Reurer Sandra, van den Hil Francijna E., Muenthaisong Suchitra, Dijke Peter ten, Mummery Christine L., *Arterioscler. Thromb. Vasc. Biol.* 2014, 34, 177.
[27] M. Greenwood-Goodwin, J. Yang, M. Hassanipour, D. Larocca, *Sci. Rep.* 2016, 6, 24403.
[28] A. Dar, H. Domev, O. Ben-Yosef, M. Tzukerman, N. Zeevi-Levin, A. Novak, I. Germanguz, M. Amit, J. Itskovitz-Eldor, *Circulation* 2012, 125, 87.
[29] V. V. Orlova, F. E. van den Hil, S. Petrus-Reurer, Y. Drabsch, P. ten Dijke, C. L. Mummery, *Nat. Protoc.* 2014, 9, 1514.
[30] I. Özen, J. Boix, G. Paul, *Clin. Transl. Med.* 2012, 1, 30.
[31] D. Ferland-McCollough, S. Slater, J. Richard, C. Reni, G. Mangialardi, *Pharmacol. Ther.* 2017, 171, 30.
[32] J. Cheng, N. Korte, R. Nortley, H. Sethi, Y. Tang, D. Attwell, *Acta Neuropathol.* (Berl.) 2018, 136, 507.
[33] G. Pettinato, X. Wen, N. Zhang, *Stem Cells Dev.* 2015, 24, 1595.
[34] J. Stenberg, M. Elovsson, R. Strehl, E. Kilmare, J. Hyllner, A. Lindahl, *Cytotechnology* 2011, 63, 227.
[35] A. Keating, *Cell Stem Cell* 2012, 10, 709.
[36] J. M. Sorrell, M. A. Baber, A. I. Caplan, *Tissue Eng. Part A* 2009, 15, 1751.
[37] A. Blocki, Y. Wang, M. Koch, P. Peh, S. Beyer, P. Law, J. Hui, M. Raghunath, *Stem Cells Dev.* 2013, 22, 2347.
[38] A. Kumar, S. S. D'Souza, O. V. Moskvin, H. Toh, B. Wang, J. Zhang, S. Swanson, L.-W. Guo, J. A. Thomson, I. I. Slukvin, *Cell Rep.* 2017, 19, 1902.
[39] A. Armulik, G. Genové, M. Mäe, M. H. Nisancioglu, E. Wallgard, C. Niaudet, L. He, J. Norlin, P. Lindblom, K. Strittmatter, et al., *Nature* 2010, 468, 557.
[40] G. Paul, I. Özen, N. S. Christophersen, T. Reinbothe, J. Bengzon, E. Visse, K. Jansson, K. Dannaeus, C. Henriques-Oliveira, L. Roybon, et al., *PLOS ONE* 2012, 7, e35577.
[41] E. A. Winkler, R. D. Bell, B. V. Zlokovic, *Mol. Neurodegener.* 2010, 5, 32.
[42] A. M. Nikolakopoulou, Z. Zhao, A. Montagne, B. V. Zlokovic, *PLOS ONE* 2017, 12, e0176225.
[43] I. Özen, T. Deierborg, K. Miharada, T. Padel, E. Englund, G. Genové, G. Paul, *Acta Neuropathol.* (Berl.) 2014, 128, 381.
[44] M. S. Thomsen, S. Birkelund, A. Burkhart, A. Stensballe, T. Moos, *J. Neurochem.* 2017, 140, 741.

We claim:
1. A method of isolating pericytes from pluripotent stem cells, the method comprising:
   a) culturing pluripotent stem cells on coated plates in a chemically defined culture medium supplemented with about 1-30 ng/ml BMP4, about 10-30 ng/ml activin and about 1-5 µM GSK-3 inhibitor for at least 2 days, b) culturing the cultured cells of step (a) in chemically defined medium supplemented with about 5-15 μg/ml transferrin, about 10-30 μg/ml insulin, about 70-150 ng/ml fibroblast growth factor 2 (FGF2), about 25-75 ng/ml vascular endothelial growth factor-A(165) (VEGF-A(165)) and about 2-10 μM TGFβ1 inhibitor sufficient to differentiate the cells into a first cell population comprising CD34− pericyte precursor cells and CD34+ endothelial progenitor cells, c) detecting the first cell population at day 6 of culture and removing the CD34+ endothelial progenitor cells from the first cell population thereby forming a second cell population comprising the CD34− pericyte precursor cells, d) culturing the second cell population comprising the CD34− pericyte precursor cells in EGM2 media for at least 2 days on coated plates thereby forming a third cell population comprising pericyte cells; and e) detecting the pericyte markers PDGFRβ, SM22, CD13 and Desmin in the third cell population comprising pericyte cells, wherein the third cell population comprises at least 95% to 99.9% pericyte cells expressing PDGFRβ and CD13.

2. The method of claim 1, wherein the pluripotent stem cells are induced pluripotent stem cells (iPSCs) or embryonic stem cells (ESCs).

3. The method of claim 1, wherein the TGFβ1 inhibitor is SB431542.

4. The method of claim 1, wherein in step (a), the chemically defined medium is supplemented with about 5 ng/ml BMP4, about 25 ng/ml activin A and about 1 μM GSK-3 inhibitor, and in step (b), the chemically defined media is supplemented with
  about 10-11 ng/ml transferrin,
  about 20 ng/ml insulin,
  about 100 ng/ml FGF2,
  about 50 ng/ml VEGF-A(165), and
  about 5 μM TGFβ1 inhibitor.

5. The method of claim 1, wherein the method does not comprise a step using feeder cell embryoid bodies.

6. The method of claim 1, wherein the second cell population comprises at least 95% CD34− cells.

7. The method of claim 1, wherein the coated plates of step (a) are solubilized basement membrane coated plates, vitronectin coated plates, fibronectin coated plates, collagen IV coated plates or a combination thereof.

8. The method of claim 1, wherein the coated plates of step (d) are selected from plates coated with gelatin, collagen, fibronectin or a combination thereof.

9. The method of claim 8, wherein the coated plates are coated with a mixture of collagen and fibronectin.

10. The method of claim 1, wherein the pericyte cells are isolated in about 8-12 days.

11. The method of claim 1, wherein the GSK-3 inhibitor is CHIR990221.

12. The method of claim 1, wherein the step (c) comprises the use of magnetic activated cell sorting.

* * * * *